(12) United States Patent
Hutchins

(10) Patent No.: US 6,264,956 B1
(45) Date of Patent: Jul. 24, 2001

(54) TUNG TREE EXTRACTS USEFUL FOR CONTROLLING TERMITES

(75) Inventor: Rachel A. Hutchins, 43 Castleberry Dr., Poplarville, MS (US) 39470

(73) Assignee: Rachel A. Hutchins, Poplarville, MS (US)

( * ) Notice: Subject to any disclaimer, the term of this patent is extended or adjusted under 35 U.S.C. 154(b) by 0 days.

(21) Appl. No.: 09/155,955

(22) PCT Filed: Apr. 30, 1997

(86) PCT No.: PCT/US97/07318

§ 371 Date: Oct. 8, 1998

§ 102(e) Date: Oct. 8, 1998

(87) PCT Pub. No.: WO97/40845

PCT Pub. Date: Nov. 6, 1997

Related U.S. Application Data

(60) Provisional application No. 60/016,682, filed on May 1, 1996.

(51) Int. Cl.$^7$ .................................................. A61K 35/78
(52) U.S. Cl. ......................................................... 424/195.1
(58) Field of Search ............................................ 424/195.1

(56) References Cited

U.S. PATENT DOCUMENTS

| | | | |
|---|---|---|---|
| 3,634,093 | * 1/1972 | Huang | 99/2 R |
| 3,839,052 | * 10/1974 | Peterson | 106/15 AF |
| 3,889,025 | * 6/1975 | Peterson | 428/413 |
| 4,293,567 | * 10/1981 | Jacobson | 424/312 |

\* cited by examiner

*Primary Examiner*—Jean C. Witz
(74) *Attorney, Agent, or Firm*—Daniel Reitenbach

(57) ABSTRACT

Termite-active extracts of the wood and kernels of the tung tree Aleurites spp., compositions thereof, and methods of use thereof.

22 Claims, 9 Drawing Sheets

US 6,264,956 B1

TUNG TREE EXTRACTS USEFUL FOR CONTROLLING TERMITES

This application is a 37 of PCT/US97/07318, filed Apr. 30, 1997 which claims priority to U.S. Provisional Application Ser. No. 60/016,682, filed May 1, 1996, entitled USING TUNG TREE (*Aleurites fordii*) EXTRACTS TO CONTROL TERMITES (RETICULITERMES SPP.).

FIELD OF THE INVENTION

This invention relates to novel termite-active extracts of tung tree (Aleurites spp.) wood and kernels (or seeds) and to compositions thereof. This invention also relates to a method for controlling termites using these extracts. More particularly, this invention relates to a method for using tung tree wood extracts as termite toxicants and deterrents and a method for using tung tree kernels as termite attractants. This invention additionally relates to an improved termite-control bait composition comprising extracts from tung tree wood and extracts from tung tree kernels.

BACKGROUND OF THE INVENTION

Subterranean termites cause millions of dollars in damages to wooden structures in the United States. This destruction is not limited to wooden structures alone—many commercial termiticides used to combat these pests are potential environmental contaminants and carcinogens. For example, the most common method of subterranean termite infestation prevention, which involves applying a chemical termiticide to a structure's peripheral grounds, often leads to soil and water contamination when applied improperly. Accordingly, it is desirable to find new means for controlling termites which do not pose such potential hazards.

Tung trees are grown in abundance in the Western Hemisphere along the Gulf Coast of the United States, particularly in the southeastern states of Louisiana, Mississippi, Alabama, Georgia and Florida, and in South America. Until the present invention, the prime commercial interest in tung trees has been in the oil which is extracted from the fruit of the plant. Tung oil is a pale yellow, pungent, drying oil composed chiefly of unsaturated fatty acid glycerides useful as a waterproofing agent and as a component of quick-drying varnishes and paints.

Two processes, mechanical and chemical, are predominantly in use in the Western Hemisphere for tung oil extraction. In the United States, the principal means of tung oil extraction involves the application of mechanical force, such as by the use of a press mill, to the tung kernels to physically squeeze the oil therefrom. This initial pressing forces about 85 percent of the oil present out of the kernels. The balance of the oil, usually about 15 percent of the original quantity, is extracted with a solvent, such as hexane. Other tung nut processing plants, principally found in South America, extract the oil by means of a 100 percent chemical process.

U.S. Pat. No. 4,293,567 describes an anti-feedant prepared from tung oil which is useful to deter boll weevils from puncturing the bolls of cotton plants.

SUMMARY OF THE INVENTION

This invention relates to a termite-active extract of the wood from the tung tree Aleurites spp., of the spurge family, Eurphorbiaceae, preferably of the species *Aleurites fordii*.

This invention also relates to a termite-active extract of the kernels from the tung tree Aleurites spp., of the spurge family, Eurphorbiaceae, preferably of the species *Aleurites fordii*.

This invention also relates to a method for controlling termites at a locus which comprises applying to the locus an effective amount of the extract of the wood from the tung tree and/or an effective amount of the extract of the kernels of the tung tree.

This invention further relates to a method for killing termites at a locus, which comprises applying to the locus a termiticidally effective amount of the extract of the wood of the tung tree. Preferably, the locus is soil, timber or other wood-based products.

This invention further relates to a method of deterring termites from feeding on a locus which comprises applying to the locus the extract of the wood from the tung tree in an amount sufficient to deter termites from feeding thereon.

This invention additionally relates to a method for attracting termites to a locus, which comprises offering to the termites at the locus, an effective attractant amount of the extract of kernels from the tung tree.

This invention further relates to a termite bait composition comprising an effective attractant amount of the extract of the kernel of the tung tree and an effective amount of a termiticide, preferably, a termiticidally effective amount of the extract of the wood of the tung tree.

DESCRIPTION OF THE INVENTION

Figure 1:
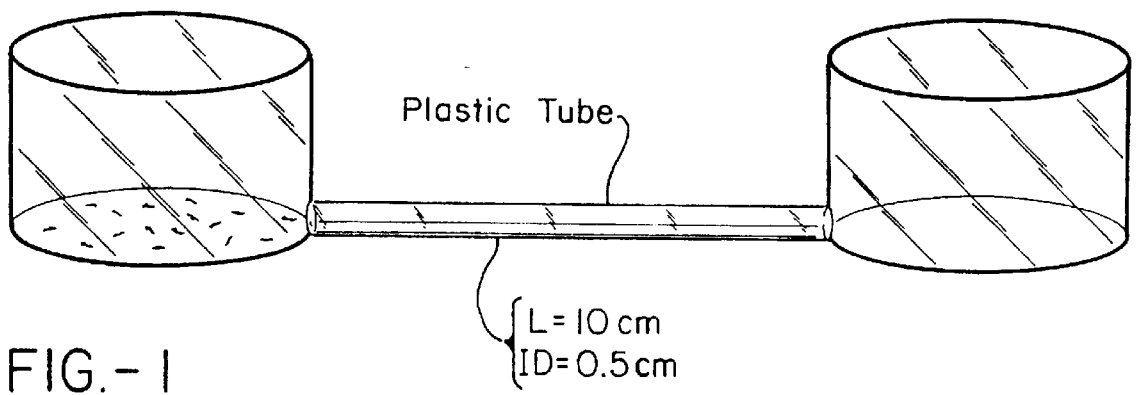
FIG. 1 is a depiction of the apparatus used in Example 4C.

The term "termite-active" means having activity against termites, such as killing, repelling, deterring and/or attracting termites.

The extracts of this invention can be obtained using standard laboratory extraction, purification, concentration, and drying methods.

The extract of the wood of the tung tree can be obtained as follows:

Wood is collected from the limbs or trunk of the tung tree, preferably with a diameter of 2 inches or larger, and the bark and cambium layers are removed. The remaining wood is then ground to a substantially fine consistency. The grinding is performed using a conventional grinding apparatus or mill and results in a finely ground powder, preferably consisting of particles having a diameter in the approximate range of about 0.1 mm to 50 mm, more preferably, about 3 mm to 10 mm.

The ground wood is added to an organic extraction solvent such as hexane, acetone, and the like, preferably a 50:50 (v/v) mixture of hexane and acetone, in a Soxhlet extractor. The percentage of ground wood in the extraction solvent is not critical as long as the resultant mixture is not packed too densely, to allow the extraction solvent to flow freely by gravity through the extractor column. The extraction solvent is allowed to cycle for an appropriate period of time, generally about 1–10 hours, preferably 4–6 hours, at a temperature above the boiling point of the extraction solvent. The resultant extraction solvent is then filtered to remove any solids. The filtered extraction solvent is then added to a rotary evaporator and heated at a temperature above room temperature, preferably at about 40° C., to remove solvent, to produce the extract.

The extract from the kernels (seeds) can be obtained as follows:

Mature nuts are harvested from the tung tree, preferably in September or October. The hull and pulp are removed from around the kernels (approximately 3–5 kernels per nut). The hard shell is then removed from the kernels to produce a meaty white embryo (the kernel "meat"). The kernel meat is then coarsely crushed and added to an organic extraction solvent such as hexane, acetone, and the like, preferably a 50:50 (v/v) mixture of hexane and acetone. The percentage of crushed kernel meat in the extraction solvent is not critical as long as the resultant mixture is liquid and flowable. The mixture of the crushed kernel meat and extraction solvent is placed in a sonic disrupter (such as an Ultrasonic Cell Disrupter) and processed, preferably at ambient temperature (approximately 25° C.), in the "pulsed" mode for about 1 minute or longer, preferably about 2 minutes. The resultant mixture is then filtered to remove the solids. The filtered mixture is then added to a rotary evaporator and heated at a temperature above room temperature, preferably at about 40° C., to remove the extraction solvent, to produce the extract.

In order to facilitate the application of the extracts of this invention to the desired locus, or to facilitate storage, transport or handling, the extracts are normally formulated with a carrier and/or a surface-active agent.

A carrier in the present context is any material with which the extract of this invention (active ingredient) is formulated to facilitate application to the locus, or storage, transport or handling. A carrier can be a solid or a liquid, including a material which is normally gaseous but which has been compressed to form a liquid. Any of the carriers normally used or known to be usable in formulating insecticidal compositions may be used.

Compositions according to the invention comprise about 0.1 to 99.9% by weight active ingredient. Preferably, compositions according to the invention comprise about 0.2 to 10.0% by weight of active ingredient, more preferably, about 0.5 to 5.0%.

Suitable solid carriers include natural and synthetic clays and silicates, for example natural silicas such as diatomaceous earths; magnesium silicates, for example talcs; magnesium aluminum silicates, for example attapulgites and vermiculites; aluminum silicates, for example kaolinites, montmorillonites and micas; calcium carbonate; calcium sulphate; ammonium sulphate; synthetic hydrated silicon oxides and synthetic calcium or aluminum silicates; elements, for example carbon and sulfur; natural and synthetic resins, for example coumaronne resins, polyvinyl chloride, and styrene polymers and copolymers; solid polychlorophenols; bitumen; waxes; agar; and solid fertilizers, for example superphosphates. Cellulose based materials, for example wood, sawdust, agar or Methocel®, as well as the other solid carriers that are themselves attractive to or at least non-repellant to termites are particularly suitable and preferable. Mixtures of different solids are often suitable. For example, a mixture of wood flour and agar formulated as a moisture containing solid would be preferable.

Suitable liquid carriers include water; alcohols, for example isopropanol and glycols; ketones, for example acetone, methyl ethyl ketone, methyl isobutyl ketone, isophorone and cyclohexanone; ethers; aromatic or aliphatic hydrocarbons, for example benzene, toluene and xylene; petroleum fractions, for example kerosene and light mineral oils; chlorinated hydrocarbons, for example carbon tetrachloride, perchloroethylene and trichloroethane; polar organic liquids, such as dimethyl formamide, dimethyl acetamide, dimethyl sulfoxide and N-methylpyrrolidone. Mixtures of different liquids are often suitable, for example a mixture of isophorone with a polar organic solvent such as N-methylpyrrolidone, as are mixtures of solid and liquid carriers.

Pesticidal compositions are often formulated and transported in a concentrated form which is subsequently diluted by the user before application. The presence of small amounts of a carrier which is a surface-active agent facilitates this process of dilution. Thus it is suitable to use at least one carrier in such a composition which is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulfonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensates of these with ethylene oxide and/or propylene oxide; condensation products of fatty alcohol or alkyl phenols, for example p-octylphenol or p-octylcresol, with ethylene oxide and/or propylene oxide; sulfates or sulfonates of these condensation products; alkali or alkaline earth metal salts, preferably sodium salts, or sulfuric or sulfonic acid esters containing at least 10 carbon atoms in the molecule, for example sodium lauryl sulphate, sodium secondary alkyl sulfates, sodium salts of sulfonated castor oil, and sodium alkylaryl sulfonates such as dodecylbenzene sulfonate; and polymers of ethylene oxide and copolymers of ethylene oxide and propylene oxide.

Compositions can, for example, be formulated as wettable powders, dusts, granules, baits, solutions, emulsifiable concentrates, emulsions, suspension concentrates and aerosols.

Wettable powders usually contain 25, 50 or 75% weight of active ingredient and usually contain in addition to solid inert carrier, 3–10% weight of a dispersing agent and, where necessary, 0–10% weight of stabilizer(s) and/or other additives such as penetrants or stickers.

Dusts are usually formulated as a dust concentrate having a similar composition to that of a wettable powder but without a dispersant, and are diluted in the field with further solid carrier to give a composition usually containing 0.5–10% weight of active ingredient.

Granules are usually prepared to have a size between 10 and 100 BS mesh (1.676–0.152 mm), and may be manufactured by, for example, agglomeration or impregnation techniques. Generally, granules will comprise about 0.1–75% weight active ingredient and 0–10% weight of additives such as stabilizers, surfactants, slow release modifiers and binding agents. The so-called "dry flowable powders" consist of relatively small granules having a relatively high concentration of active ingredient. Of particular interest in current practice are the water dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulation contain 90% or more by weight of finely divided active material, 3–7% by weight of a blend of surfactants, which act as wetting dispersing, suspending and binding agents, and 1–3% by weight of a finely divided carrier, which acts as a resuspending agent.

Baits are prepared by, for example, combining a mixture of a finely divided cellulose material, such as sawdust, with an amount of ingredient(s) sufficient to provide the desired result; for example, from about 0.1% to about 20% weight, preferably about 0.2 to about 5%, active ingredient(s) and forming the mixture into a paste by the addition of about 1% to 5% of a water based binder such as agar. The paste-like mixture is packed into a housing such as a hollowed out wooden dowel. Baits are a preferable embodiment of the present invention.

Wood or timber is impregnated with active ingredient according to well known procedures including pressure treatments such as the Lowery empty cell process and full cell process, vacuum treatments, hot and cold bath treatment, thermal treatment, and cold-soak treatment. Surface treatment of wood or timber is accomplished by well known techniques such as brushing, dipping, spraying or short-soaking the wood material with active ingredient or appropriate compositions thereof in amounts and in a manner that would be apparent to one skilled in the art.

For instance, wood treatments may be accomplished by two major methods: impregnation of the wood through vacuum and pressure treatments and surface treatments such as painting, spraying or dipping. In an impregnation method, a concentrate may be formulated which comprises about 1–65% weight per volume active ingredient, 5–50% solvent and, when necessary, co-solvent, and 0–20% w/v of other additives such as penetrants. For treatment, vacuum is pulled on a vessel containing the wood. The concentrate is then added to the vessel and subsequently pressurized to force concentrate into the wood. The vessel is relieved of pressure and the treated wood then removed. In a surface treatment, the concentrate may be simply painted onto a wood surface by means of brushing or spraying or, preferably, dipping. Solvents used for these types of treatments may include polyethylene glycol, and aromatic solvents, and the like due to their ability to penetrate wood.

Emulsifiable concentrates usually comprise, in addition to a solvent and, when necessary, co-solvent, about 10–50% weight per volume active ingredient, 2–20% weight per volume emulsifiers and 0–20% weight per volume of other additives such as stabilizers, penetrants and corrosion inhibitors.

Suspension concentrates are usually compounded so as to obtain a stable, non-sedimenting flowable product and usually comprise about 10–75% weight active ingredient, 0.5–15% weight of dispersing agents, 0.1–10% weight of suspending agents such as protective colloids and thixotropic agents, 0–10% weight of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions are compositions which may be obtained by diluting a wettable powder or a concentrate with water. The said emulsions may be of the water-in-oil or of the oil-in-water type, and may have a thick 'mayonnaise'-like consistency.

Compositions can also comprise other ingredients, for example, further active compounds possessing herbicidal, insecticidal or fungicidal properties, in accordance with the requirement of the locus to be treated and the treatment method.

The method of applying an extract of this invention to combat termites comprises applying the extract, conveniently in a composition comprising the extract of this invention and a carrier as described above, to a locus or area to be treated for the termites, such as soil or timber, already subject to infestation or attack by termites or intended to be protected from infestation by termites. The active ingredient is, of course, applied in an amount sufficient to effect the desired action of combatting termite infestation. This dosage is dependent upon many factors, including the carrier employed, the method and conditions of the application, whether the formulation is present at the locus in the form of a film, or as discrete particles or as a bait, the thickness of film or size of particles, the degree of termite infestation, and the like.

Proper consideration and resolution of these factors to provide the necessary dosage of the active ingredient at the locus to be protected are within the skill of those versed in the art. In general, however, the effective dosage of the compound of the invention at the locus to be protected (i.e., the dosage to which the termite has access) is of the order of about 0.1 to 10.0% based on the total weight of the composition, preferably, about 0.2% to 5%.

In one embodiment of this invention, the extracts of this invention are used to combat termites in the soil, thereby achieving indirect protection for any timber-based constructions erected on the treated soil or to crops, grassland, forestry (especially young saplings), and other cellulose based materials surrounded by or located in the treated soil. Suitable soil-based control of termites is obtained by providing in the soil an effective dosage of an extract of this invention. For use in this manner, the active ingredient is suitably applied to the soil at a rate of from about 0.01 gram to about 10 kilograms per hectare. Depending on the composition used, good control of soil inhabiting termites is obtained at rates of from about 0.01 gram to about 1 kilogram per hectare and preferably from about 0.1 gram to 100 grams per hectare. The extract of this invention can conveniently be formulated for use as a extract-impregnated wooden stake, bait, granule or powder containing a solid diluent, or as a suspension concentrate. Such formulations generally comprise from about 0.1 to about 50% by weight of the active ingredient. Effective control results when the formulation is physically integrated into the topsoil as well as when it is applied to the surface of the soil.

The extracts of this invention can also be applied as a drench, i.e., as a solution or dispersion of the compound in a suitable solvent or liquid diluent. Such drenches can be prepared by diluting with water a concentrate containing the extract of this invention, an emulsifying agent, and preferably an organic solvent, such as isophorone and/or N-methylpyrrolidone. The extract of this invention can be applied by band, furrow or side-dress techniques, and may be incorporated or not.

In another embodiment of the invention, the extracts of this invention are applied directly on or into the material to be protected or treated. For example, timber is treated either before, during or after its incorporation into a structure or building, thereby protecting it against damage from termite attack or combating an already existing infestation of termites. For treatment of timber, the composition can contain a penetrant designed to facilitate penetration of the active ingredient to a significant depth in the timber, thereby ensuring that superficial-surface abrasion will not generate a surface free from active ingredient and thus vulnerable to termite penetration.

Examples of materials known for use as wood penetrants include paraffinic hydrocarbons, for instance low aromatic white spirit, 2-ethoxyethanol and methyl isobutyl ketone. Preferably the penetrant is 2-ethoxyethanol or methyl isobutyl ketone, optionally in association with isophorone and/or N-methyl pyrrolidone. It is useful in such timber treatment to incorporate "anti-bloom" agent, which counteract the tendency for the active ingredient to migrate to the surface ("blooming"), suitable materials being dibutyl phthalate and o-dichlorobenzene.

Timber treatment compositions can also, if desired, contain fungicides (to prevent fungal attacks such as dry rot and wet rot), and/or pigments in order to combine termite protection with painting of the timber. In this context, painting will be understood to include not only the application of covering pigmentation (commonly white), but also the application of natural wood coloration in order to restore the appearance of weathered timber (e.g., as with treatments to red cedar external housing timbers).

The actual application onto or into the timber may be carried out using conventional techniques including immersion of the timber in the liquid, painting the liquid onto the timber by spray or brushing, and injecting the liquid into the timber.

The concentration of active ingredient in the treated timber should, of course, be sufficient to achieve the desired effect. However, the total volume of formulated product taken up by the timber is limited by the absorption properties of the wood with respect to that formulation and will also vary according to the application procedure adopted (immersing, painting or injecting); hence the concentration of active ingredient in the formulation should be such as to produce the desired concentration in the treated timber. The formulation may be aqueous, as for example obtained by dilution of a conventional insecticide emulsifiable concentrate, or non-aqueous such as an undiluted emulsifiable concentrate. The organic solvent in such formulations will suitably be one of those previously described.

The determination of the necessary parameters applicable to specific types of wood and particular treatment procedures can readily be determined by established techniques conventionally used by those skilled in the art.

The following examples are provided to illustrate the invention.

EXAMPLE 1
Preparation of Tung Wood Extract
Wood was collected from the limbs or trunk of the tung tree (Aleurites fordii) with a diameter of 2 inches or larger, and the bark and cambium layers were removed. The remaining wood was then ground using a conventional grinding mill into particles having a diameter of about 3 mm to 10 mm.

The ground wood was added to an extraction solvent of 50:50 (v/v) mixture of hexane and acetone, in a Soxhlet extractor. The extraction solvent was allowed to cycle for 4–6 hours at a temperature above the boiling point of the extraction solvent. The resultant extraction solvent was then filtered through a Whatman filter to remove any solids. The filtered extraction solvent was then added to a rotary evaporator to remove the solvent, maintaining the bath temperature of the evaporator bulb at 40° C., to yield 2–5% by weight of the tung wood extract.

EXAMPLE 2
Preparation of the Kernel Extract
Mature nuts were harvested from the tung tree (Aleurites fordii), in September/October. The hull and pulp were removed from around the kernels (approximately 3–5 kernels per nut). The hard shell was then removed from the kernels to produce a meaty white embryo (the kernel "meat"). The kernel meat was then coarsely crushed and added to an extraction solvent of 50% hexane and 50% acetone (v/v). The mixture of the crushed kernel meat and extraction solvent was placed in an Ultrasonic Cell Disrupter and processed at ambient temperature (approximately 25° C.), in the "pulsed" mode for 2 minutes. The resultant mixture is then filtered using Whatman filter paper to remove the solids. The filtered mixture was then added to a rotary evaporator to remove the solvent, maintaining the bath temperature of the evaporator bulb at 40° C., to yield 25–30% by weight of the kernel extract. The kernel extract was yellow, oily to the touch, with a slightly pungent aroma.

EXAMPLE 3
Efficacy of Tung Wood Extract and Kernel Extract
The extracts obtained as described above in Examples 1 and 2 were diluted with acetone to the followings concentrations (w/v): 0.125%, 0.25%, 0.5%, 1% and 2%.

Pine stakes (4"×1"×¼") were vacuum impregnated at 690 mm for approximately 5 minutes using the following solutions:
1. Acetone alone
2. Hexane alone
3. Acetone/Hexane 50:50 (v/v)
4. 2% Wood Extract in acetone (w/v)
5. 2% Kernel Extract in acetone (w/v)
6. Wood Extract/Kernel Extract Combinations in acetone (w/v): 0.125%/0.125%, 0.25%/0.25%, 0.5%/0.5%, 1%/1%, and 2%/2%.

5 pine stakes were impregnated with each of the above solutions. One set of 5 pine stakes was left untreated as used as a control.

The stakes were weighed immediately after treatment and then again after the stakes had dried, to determine the extract retention.

5 stakes (4"×1"×¼") of tung tree wood were cut and weighed.

The stakes (pine and tung tree wood) were randomly placed into shaded, moist ground, spaced about 1 foot apart and about ⅔ length pushed in. The stakes were left for about 5 months, then removed, cleaned and weighed. Consumption of each stake was determined by its decrease in weight.

Figure 7:
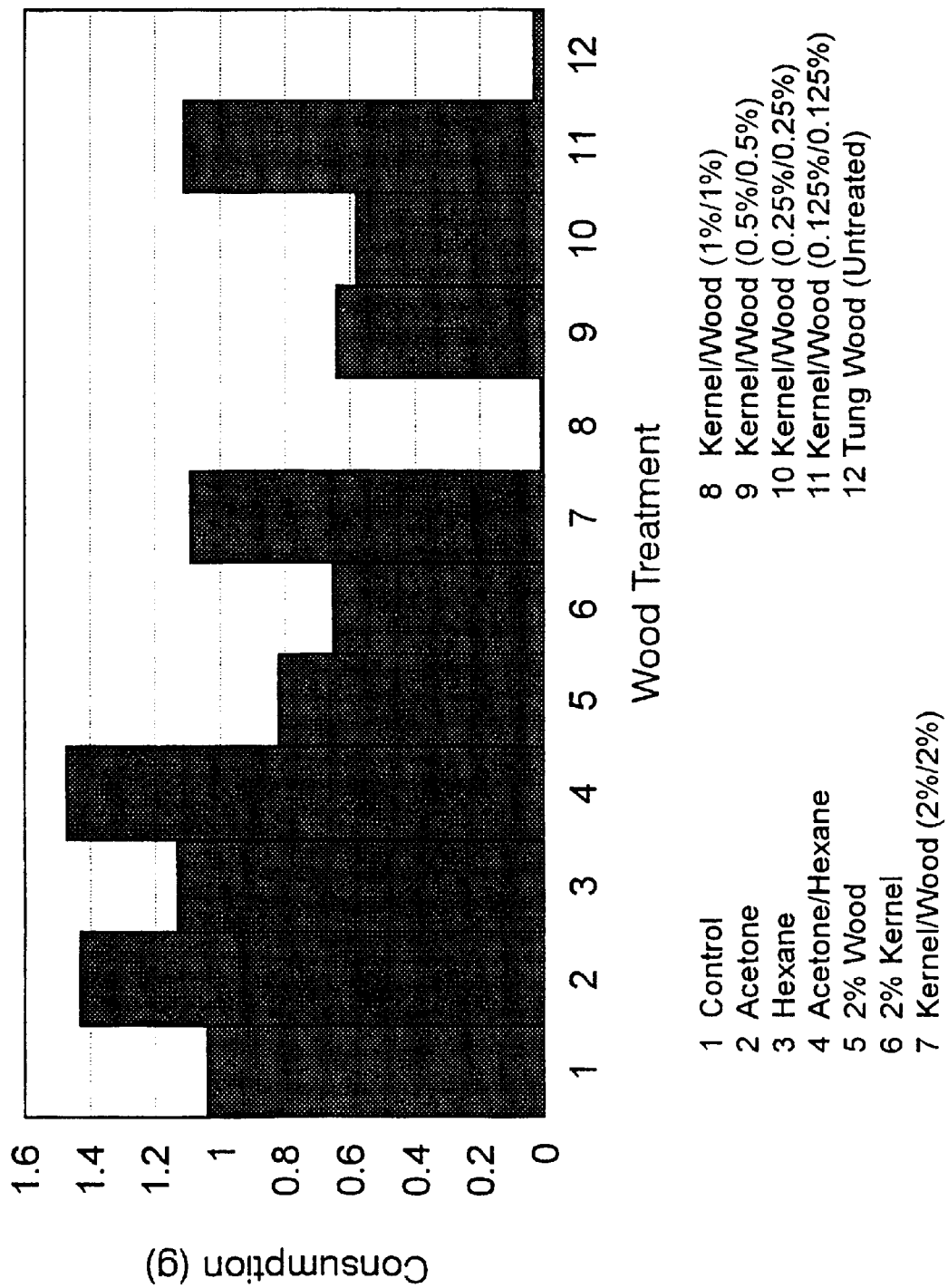
FIG. 7 is a graphic representation of the results obtained in Example 3.

The results of this testing are presented in Table 1 below and in FIG. 7.

TABLE 1

Effect of Treatment on Consumption of Pine Stakes

| Treatment | Consumption (grams) (Average of 5 stakes) |
|---|---|
| Control (No treatment) | 1.04 |
| Acetone | 1.43 |
| Hexane | 1.13 |
| Acetone/Hexane (50/50) | 1.47 |
| 2% Wood Extract | 0.82 |
| 2% Kernel Extract | 0.65 |
| Kernel/Wood (2%/2%) | 1.09 |
| Kernel/Wood (1%/1%) | 0.00 |
| Kernel/Wood (0.5%/0.5%) | 0.64 |
| Kernel/Wood (0.25%/0.25%) | 0.58 |
| Kernel/Wood (0.125%/0.125%) | 1.11 |
| Tung Wood (No treatment) | 0.03 |

EXAMPLE 4

Wood extract and kernel extract were obtained as described in Examples 1 and 2 and diluted with acetone to the following concentrations (w/v): 0.1%, 1%, 2.5% and 5.0%.

In the tests described below, externally undifferentiated worker Eastern subterranean termites (*Reticulitermes flavipes*) beyond the third instar were used. All tests were conducted in triplicate.

A. No-Choice Test

Aliquots (1 ml) of each of the above diluted extracts were topically applied to 0.5 g cellulose pads. Each pad was then moistened, placed into a small cylindrical plastic container (4.0 cm×5.3 cm), and exposed to a group of 25 termites for 25 days.

Figure 4:
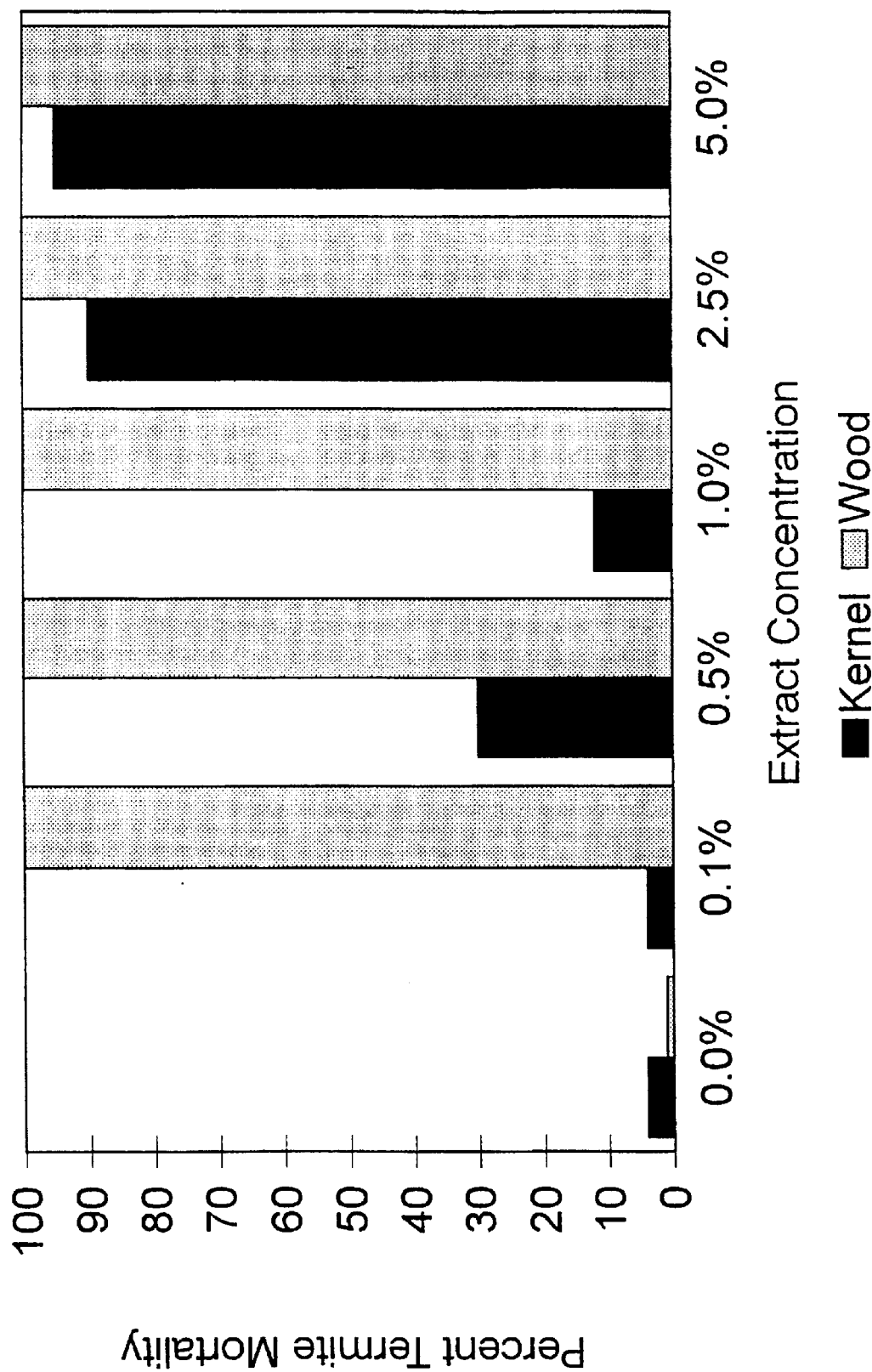
FIG. 4 is a graphic representation of the results obtained in Example 4A.

The mortality rates of the termites were monitored. The mortality rates (in percentages) are shown in FIG. 4.

B. Repellency Test

Figure 5:
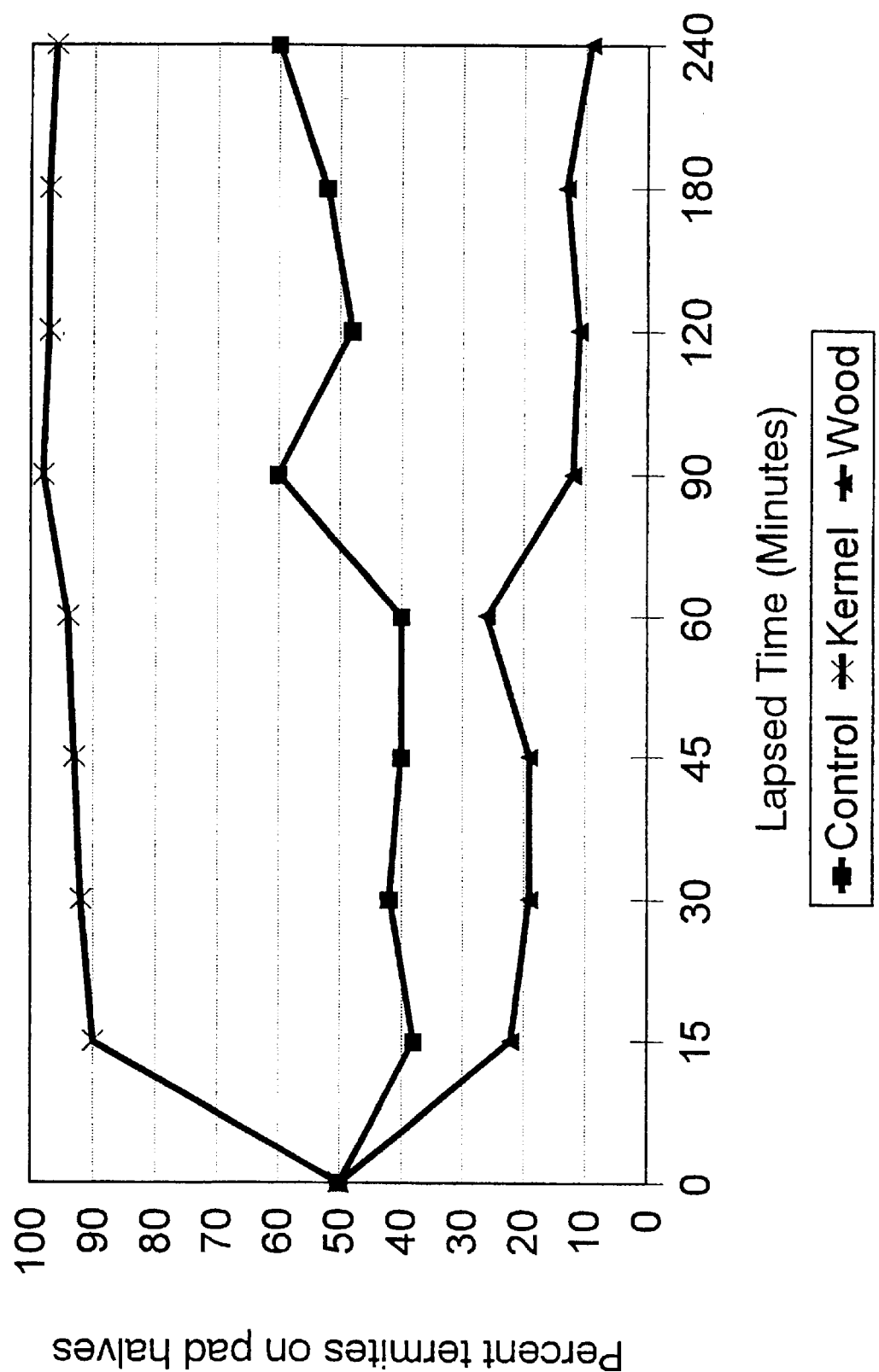
FIG. 5 is a graphic representation of the results obtained in Example 4B.

Groups of ten (10) termites were added to small containers containing extract-treated cellulose pad halves paired with untreated pad halves. The location of the termites was noted at eight time intervals from 15 to 240 minutes. The results of this test is shown in FIG. 5.

C. Choice Test

The apparatus for this test was constructed as depicted in FIG. 1.

Figure 6:
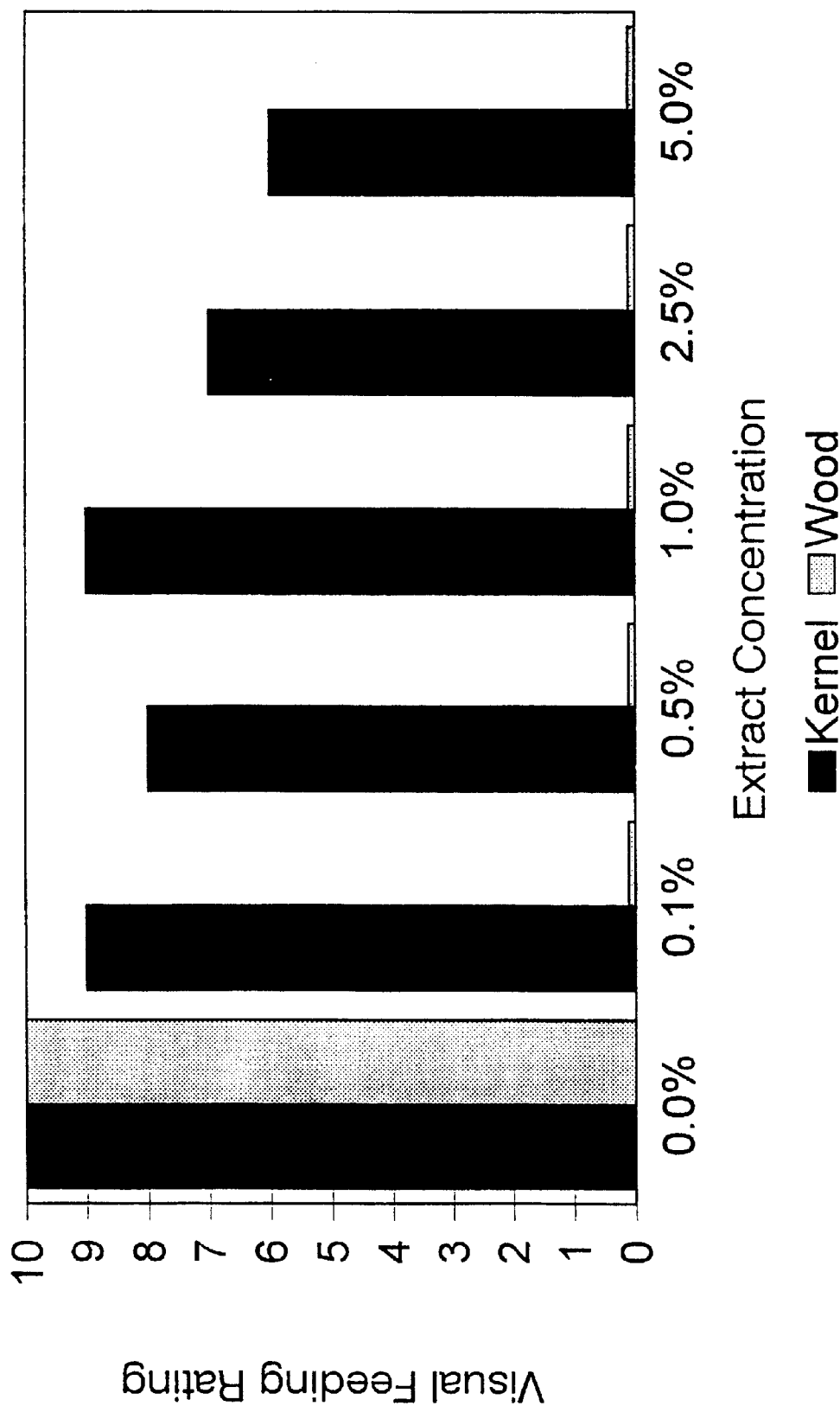
FIG. 6 is a graphic representation of the results obtained in Example 4C.

One chamber contained an untreated cellulose pad. A cellulose pad was dyed blue and topically treated with extract was placed in the other chamber. The blue dye served as a feeding indicator because it became visible in the termites' hindguts after consumption of the treated pad. Twenty-five (25) termites were introduced via the chamber with the treated pad, although their movement through the test apparatus was not restricted. Daily througout the 8 day test period, a visual feeding rating from 0 to 10 was assigned to the termites based on the intensity of the blue color of their hindguts, with 0 being no color and 10 being the highest intensity of blue color. The results of this test are shown in FIG. 6.

EXAMPLE 5

Wood and Kernal Combinations as Termite Bait Compositions

Wood extract and kernel extract were obtained as described in Examples 1 and 2 and diluted with acetone to the following concentrations (w/v): 0.1%, 1%, 2.5% and 5.0%.

A. Repellency Test

Figure 8:
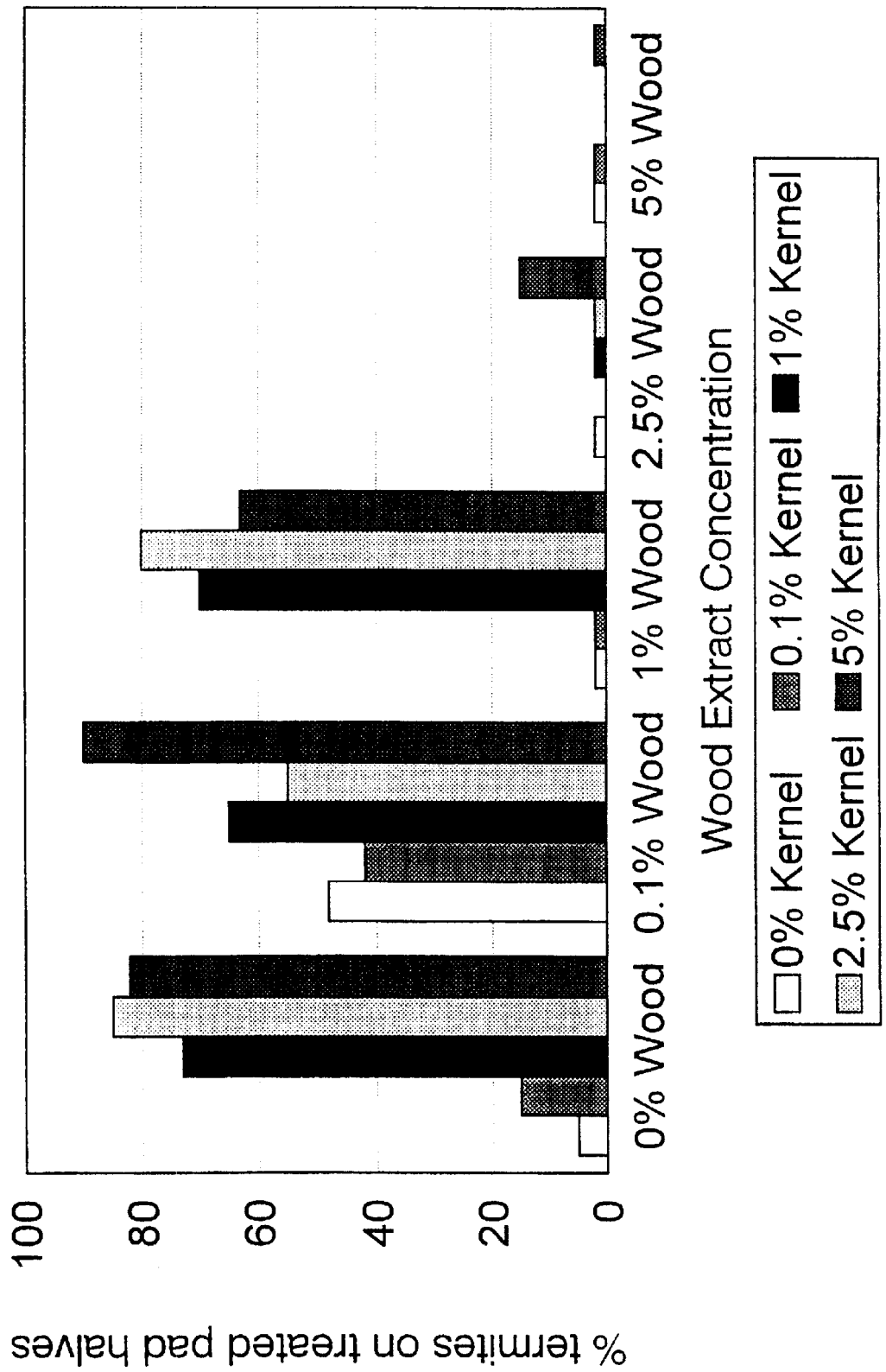
FIG. 8 is a graphic representation of the results obtained in Example 5A.

The Repellency Test was conducted as described above in Example 4B using 25 different wood/kernal extract combinations, and monitored for one hour. The combinations of the dilutions of the wood and kernel extracts were as described below in Table 2. The results of this test are shown in Table 2 and in FIG. 8.

TABLE 2

Combinations of Dilutions of Wood and Kernal Extracts (1:1 v/v)

| Combination No. | Wood Extract (%) | Kernel Extract (%) | % Termites on Treated Pad Halves |
|---|---|---|---|
| 1 | 0 | 0 | 5 |
| 2 | 0 | 0.1 | 15 |
| 3 | 0 | 1 | 73 |
| 4 | 0 | 2.5 | 85 |
| 5 | 0 | 5 | 82 |
| 6 | 0.1 | 0 | 48 |
| 7 | 0.1 | 0.1 | 42 |
| 8 | 0.1 | 1 | 65 |
| 9 | 0.1 | 2.5 | 55 |
| 10 | 0.1 | 5 | 90 |
| 11 | 1 | 0 | 2 |
| 12 | 1 | 0.1 | 2 |
| 13 | 1 | 1 | 70 |
| 14 | 1 | 2.5 | 80 |
| 15 | 1 | 5 | 63 |
| 16 | 2.5 | 0 | 2 |
| 17 | 2.5 | 0.1 | 0 |
| 18 | 2.5 | 1 | 2 |
| 19 | 2.5 | 2.5 | 2 |
| 20 | 2.5 | 5 | 15 |
| 21 | 5 | 0 | 2 |
| 22 | 5 | 0.1 | 2 |
| 23 | 5 | 1 | 0 |
| 24 | 5 | 2.5 | 0 |
| 25 | 5 | 5 | 2 |

B. Choice Test

Using the combinations of wood and kernel extract dilutions as described in A above, the Choice Test as described above in Example 4C was conducted.

In this test, as the concentration of the wood extract increased, the termite mortality rate increased, and the feeding on the treated pads decreased.

C. Choice Test Using Combination of 1% Wood Extract and 1% Kernel Extract

Figure 9:
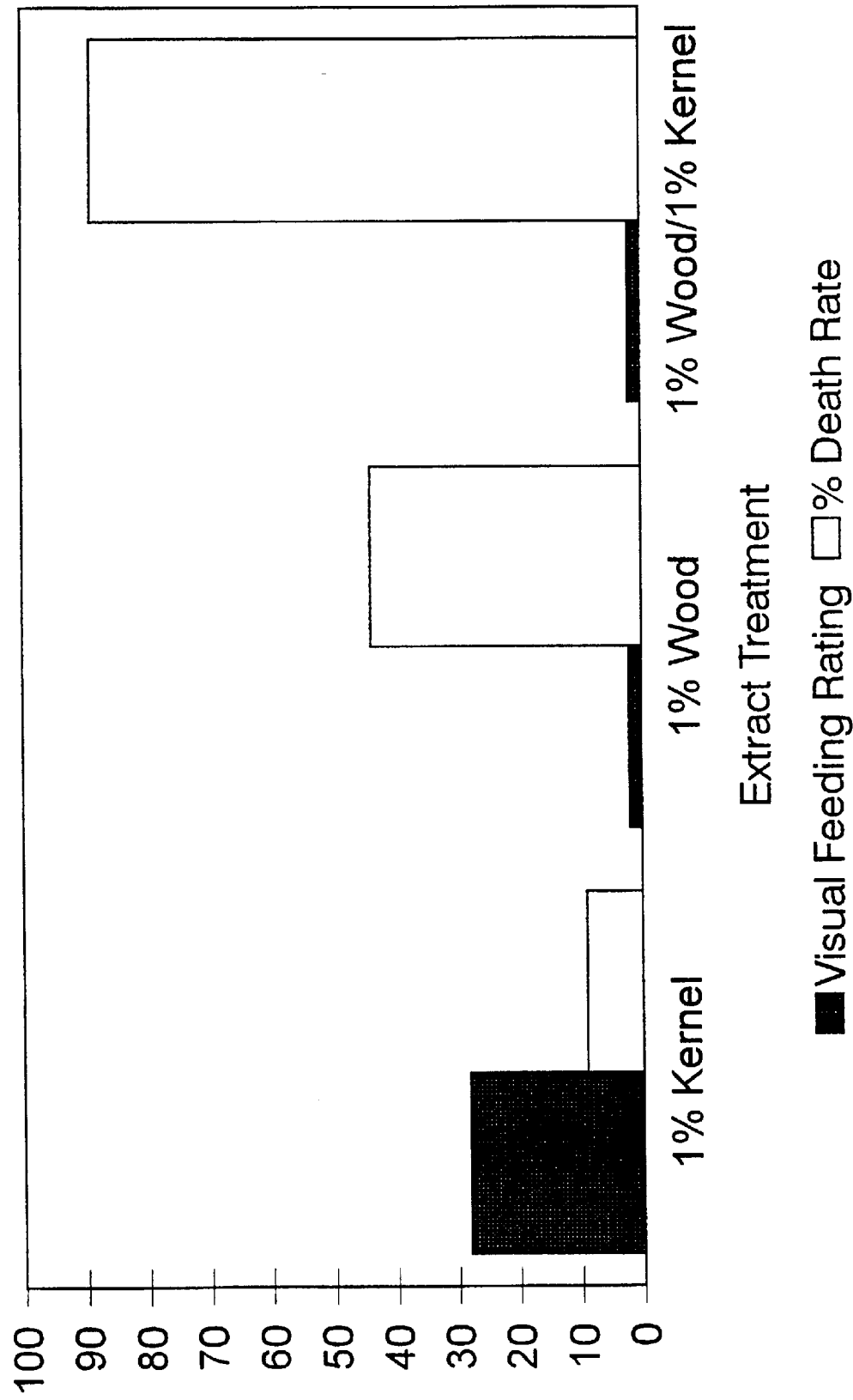
FIG. 9 is a graphic representation of the results obtained in Example 5C.

The Choice Test described above in Example 4C was conducted using 1% wood extract, 1% kernel extract, and a combination of 1% wood extract and 1% kernel extract. The comparative termite mortality results of this test are shown in FIG. 9.

EXAMPLE 6

Paired blocks of Southern yellow pine in a sand medium were placed in large plastic containers. One block of each pair was left untreated, while the other block was topically treated with kernel extract in three different concentrations (0.2%, 1.0%, and 5.0%) plus a control (0.0%). 5 replications were performed. The kernel extract dilutions were prepared as described in Example 3 above. Differences in consumption of the treated and untreated blocks were examined by comparing pre- and post-test block weights.

Figure 10:
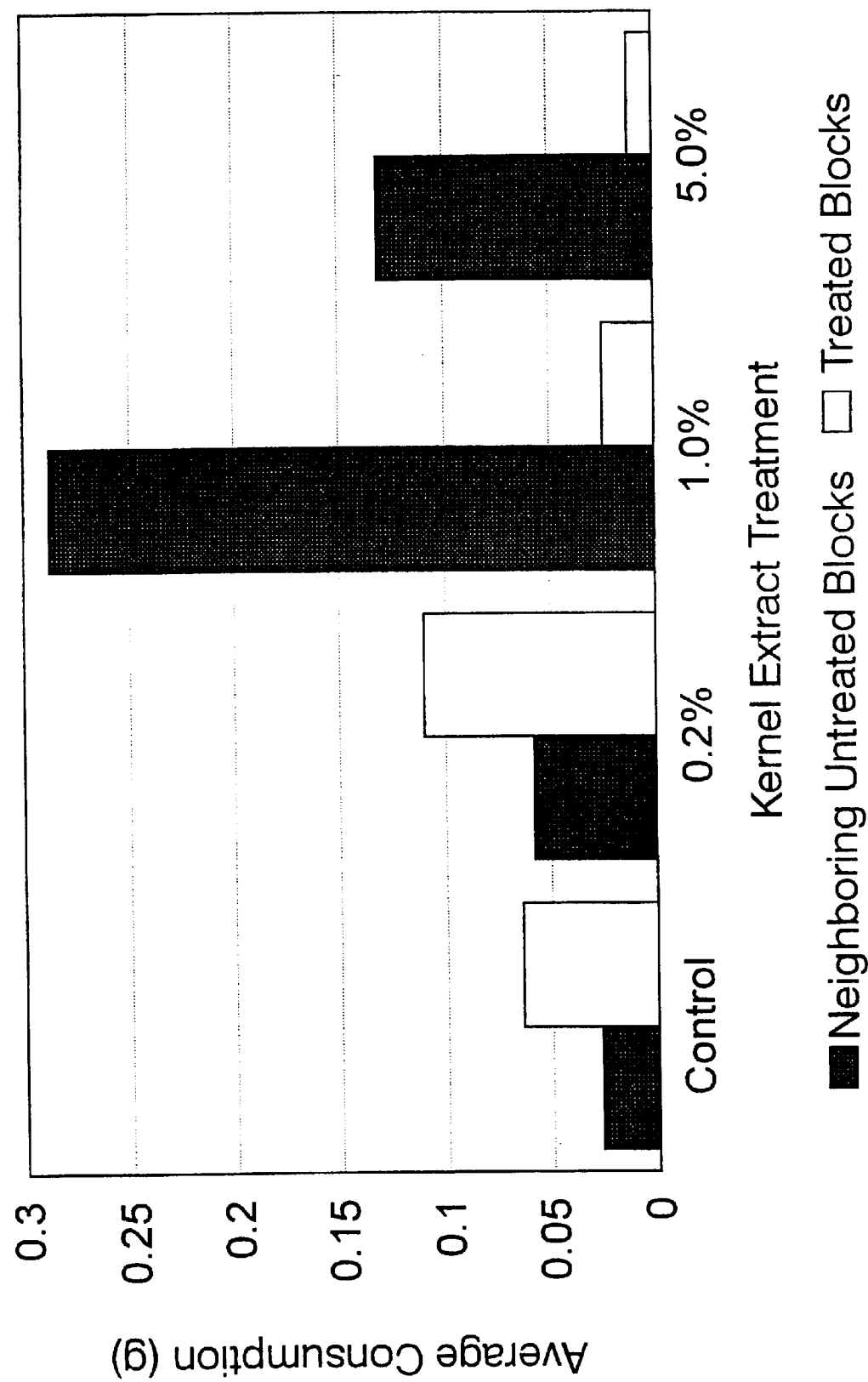
FIG. 10 is a graphic representation of the results obtained in Example 6.

As shown in FIG. 10, termites consumed 10.9 times more wood in the untreated blocks paired with 1% kernel extracted treated blocks than in those blocks paired with the control (solvent-treated) blocks. In contrast, as seen in FIG. 10, termites' feeding on the extract-treated blocks was not significant.

Additionally, tunneling activity was visually analyzed and was found to be more prevalent near the 1% kernel/untreated pairs than near the control/untreated pairs.

EXAMPLE 7

Figure 2:
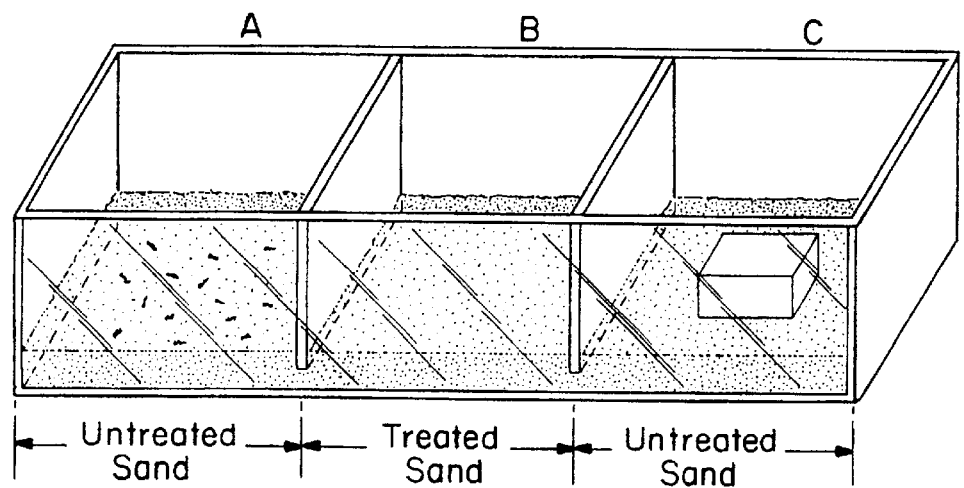
FIG. 2 is a depiction of the apparatus used in Example 7.

One hundred (100) termites were placed at one end of the three-chambered container depicted in FIG. 2, with a food source (an untreated pine block) at the opposite end. In order to reach the food source, the termites had to tunnel through the center chamber, which contained untreated sand, 1% wood extract-treated sand, or 5% wood extract-treated sand. Plastic barriers prevented termites from crossing over the sand.

All termites in the control box, which had the untreated sand barrier, reached the food source within the first 6 hours. In contrast, no termites in the boxes containing either the 1% or 5% wood extract-treated sand ever reached the food source. All the termites were dead within 10 days.

EXAMPLE 8

Figure 3:
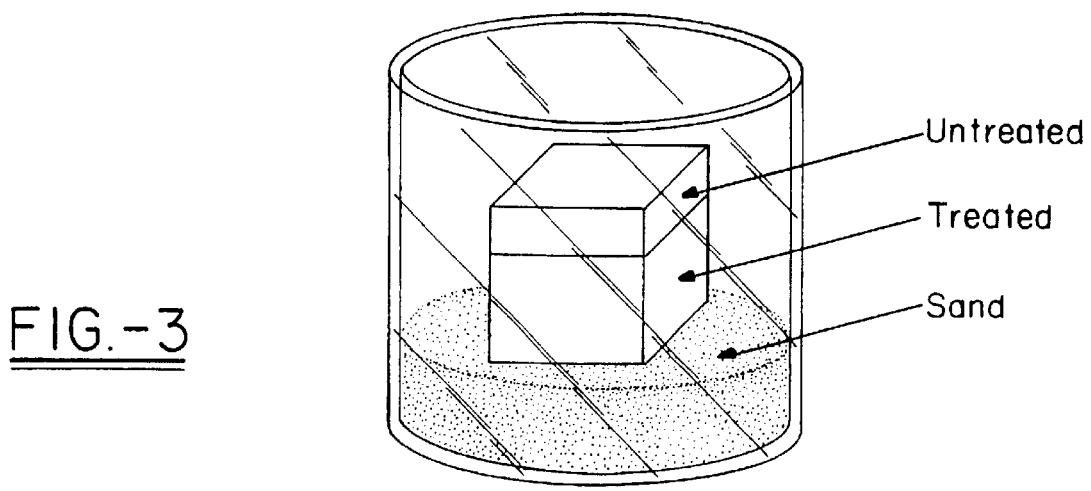
FIG. 3 is a depiction of the apparatus used in Example 8.

Using the apparatus depicted in FIG. 3, stacked blocks of Southern yellow pine were placed in sand in individual containers which held 100 termites each. The bottom block (1.270 cm×1.905 cm×1.905 cm) was either an untreated block (control), a 0.2% wood extract-treated block, a 1% wood extract-treated block, or a 5% wood extract-treated block. The top block was an untreated block (0.635 cm×1.905 cm×1.905 cm). The wood extract-treated blocks were treated with a topical spray of the wood extract. Consumption of the top blocks was measured after 31 days to determine if the wood extract treatment of the bottom blocks would prevent or reduce termite consumption of the top untreated blocks.

Figure 11:
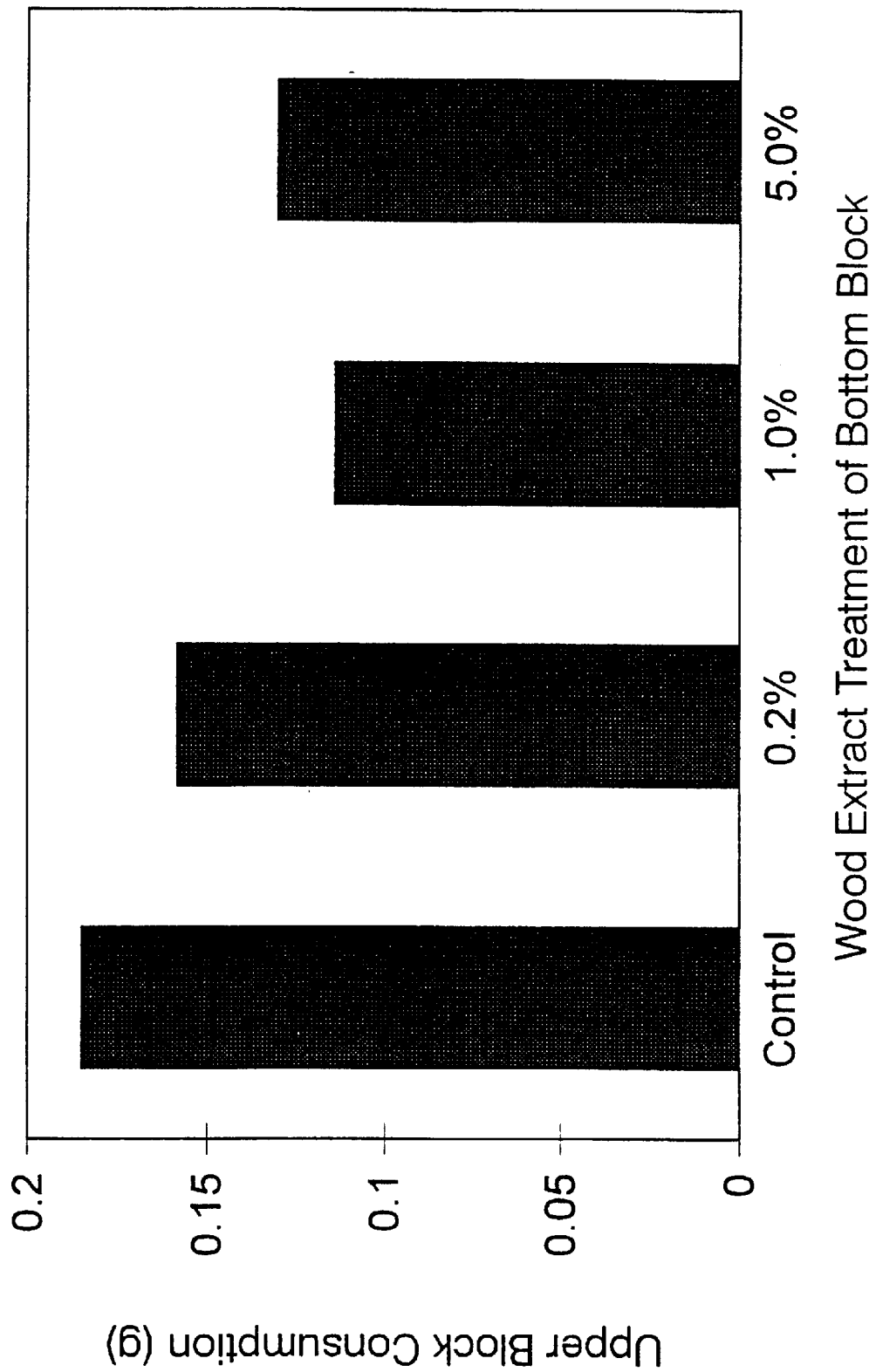
FIG. 11 is a graphic representation of the results obtained in Example 8.

As seen in FIG. 11, consumption of the control blocks was significantly higher than that of the untreated blocks placed on top of the 1% and 5% wood extract-treated blocks.

What is claimed is:

1. A termite-active extract of the wood from the tung tree Aleurites spp., of the spurge family, Eurphorbiaceae.

2. An extract as recited in claim 1 wherein the tung tree is of the species *Aleurites fordii*.

3. A method for controlling termites at a locus which comprises applying to the locus an effective amount of the extract of claim 1.

4. A method as recited in claim 3 wherein the locus is soil or timber.

5. A method for controlling termites at a locus which comprises applying to the locus an effective amount of the extract of claim 2.

6. A method as recited in claim 5 wherein the locus is soil or timber.

7. A method for controlling termites at a locus which comprises applying to the locus an effective amount of the extract of claim 1 and the extract of claim 2.

8. A method of deterring termites from feeding on a locus which comprises applying to the locus the extract of claim 1 in an amount sufficient to deter termites from feeding thereon.

9. A method for attracting termites to a locus, which comprises offering to the termites at the locus, an effective attractant amount of a termite-active extract of the kernels from the tung tree Aleurites spp., of the spurge family Eurphorbiaceae.

10. A termite bait composition comprising an effective attractant amount of a termite-active extract of the kernels from the tung tree Aleurites spp., of the spurge family Eurphorbiaceae, and an effective amount of a termiticide.

11. A termite bait composition as recited in claim 10 wherein the termiticide is a termiticidally effective amount of the extract of the wood from the tung tree Aleurites spp., of the spurge family, Eurphorbiaceae.

12. A composition comprising an effective amount of the extract as recited in claim 1 and a suitable carrier.

13. A composition comprising an effective amount of the extract as recited in claim 2 and a suitable carrier.

14. A composition comprising an effective amount of the extract as recited in claim 1, an effective amount of a termite-active extract of the kernels from the tung tree Aleurites spp., of the spurge family Eurphorbiaceae, and a suitable carrier.

15. A method for controlling termites at a locus which comprises applying to the locus an effective amount of the composition of claim 12.

16. A method as recited in claim 15 wherein the carrier comprises wood.

17. A method for controlling termites at a locus which comprises applying to the locus an effective amount of the composition of claim 13.

18. A method as recited in claim 17 wherein the carrier comprises wood.

19. A method for controlling termites at a locus which comprises applying to the locus an effective amount of the composition of claim 14.

20. A method as recited in claim 19 wherein the carrier comprises wood.

21. A method for attracting termites to a locus which comprises applying to the locus an effective amount of a composition containing a termite-active effective amount of a termite-active extract of the kernels from the tung tree Aleurites spp., of the spurge family Eurphorbiaceae, and one or more non-termite-active carriers or diluents.

22. A method as recited in claim 21 wherein the carrier comprises wood.

* * * * *